Figure 1:
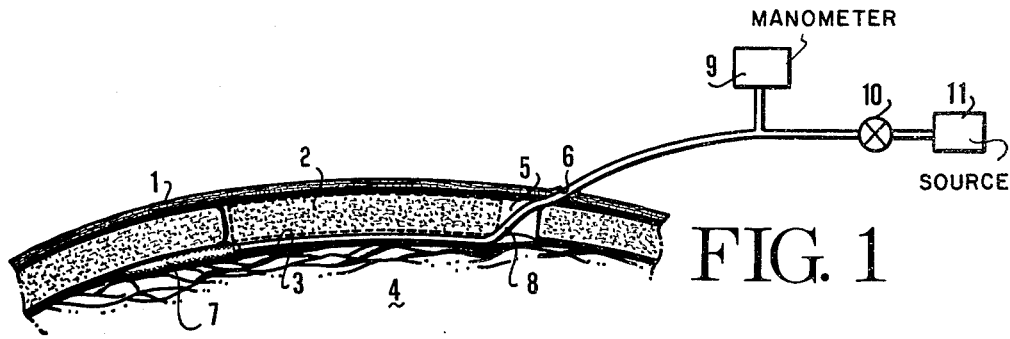

United States Patent [19]

Ikebe et al.

[11] 4,147,161
[45] Apr. 3, 1979

[54] INTRACRANIAL PRESSURE MONITORING METHOD AND SYSTEM

[75] Inventors: Jun Ikebe; Yoriaki Kumagai; Kintomo Takakura, all of Tokyo; Michio Ohta, Yokohama, all of Japan

[73] Assignee: Clinical Engineering Laboratory Limited, Tokyo, Japan

[21] Appl. No.: 827,740

[22] Filed: Aug. 25, 1977

[30] Foreign Application Priority Data

Aug. 27, 1976 [JP] Japan ............................... 51-102399

[51] Int. Cl.² .............................................. A61B 5/00
[52] U.S. Cl. ...................................... 128/2 R; 73/731
[58] Field of Search ......... 128/2 R, 2 N, 2 S, 2.05 D, 128/2.05 E, 350 R, 350 V, 2.08; 73/715, 731

[56] References Cited
U.S. PATENT DOCUMENTS

| 327,403 | 9/1885 | McDonnell | 128/2.08 |
| 3,598,106 | 8/1971 | Buning | 128/2 S |
| 3,789,667 | 2/1974 | Porter et al. | 128/2.05 D X |
| 3,958,562 | 5/1976 | Hakim et al. | 128/2 R |
| 4,006,735 | 2/1977 | Hittman et al. | 128/2.05 E X |

OTHER PUBLICATIONS

Kunov, et al., "A Hydraulic Pouch . . . Dynamics", MBE, Jan. 1975, vol. 13, No. 1, pp. 65-70.
Eversden, "Modifications . . . Intracranial Pressure", MBE, vol. 8, pp. 159-164, 1970.

Primary Examiner—Lee S. Cohen
Attorney, Agent, or Firm—Martin A. Farber

[57] ABSTRACT

System for measuring or monitoring the intracranial pressure which comprises a non-elastic detecting pouch to be inserted into the space between the skull and the cerebrum, a flexible tube connected to the pouch, a device for supplying a liquid into the pouch through the flexible tube and a device for measuring the pressure of the liquid in the pouch. When the pressure of the liquid reaches the intracranial pressure, the curve showing relation between liquid pressure vs. pouch volume flattens. Thus, by measuring the pressure of the flattened region, intracranial pressure may be determined.

6 Claims, 5 Drawing Figures

U.S. Patent     Apr. 3, 1979     4,147,161

INTRACRANIAL PRESSURE MONITORING METHOD AND SYSTEM

The present invention relates to a system to monitor the intracranial pressure of postoperative patients. To measure the pressure of the intracranial region, e.g. ventricle or subdural and epidural parts, several methods are in current use in which a pneumatic balancing device or a wireless electronic frequency modulation device comprising a transmitter and a receiver is used. An air supplying device must be provided in the former method which complicates the system and consequently raises the cost of the equipment. While the latter has the merit of inplantability of the transmitter as a pressure detector, it is not suitable for short term monitoring because a surgical procedure is necessary for removing the transmitter. What is worse still, when the patient turns around in bed, there occurs a large amount of drift in the pressure indications in either system.

It is an object of the present invention to overcome above-mentioned problems, which features the utilization of a liquid-filled pouch as a detector to transduce the intracranial pressure into hydraulic pressure which is then measured by a semiconductor-type manometer through a slender tube. This system has a high speed response, high accuracy without drifting of the indication due to turning of the patient. Furthermore, the pouch, which is disposable and of very low cost, is easily extracted without a surgical procedure.

Figure 2:
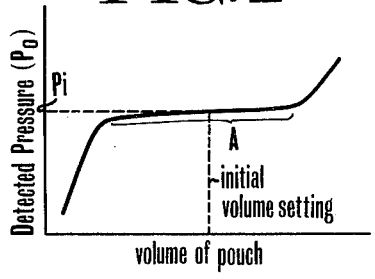
Figure 3:
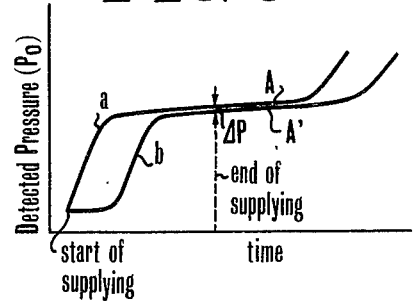
Figure 4:
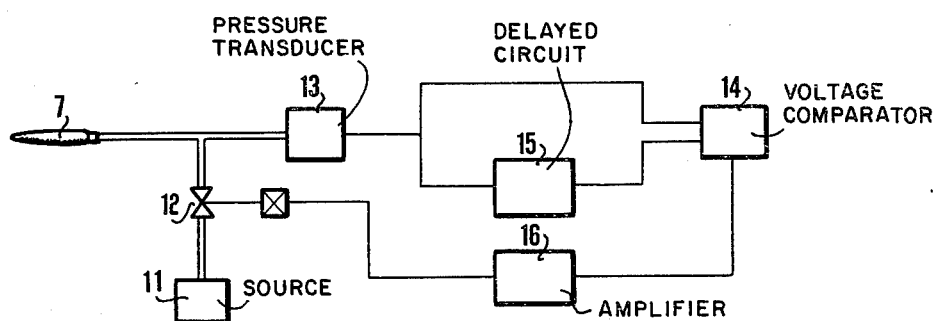
Figure 5:
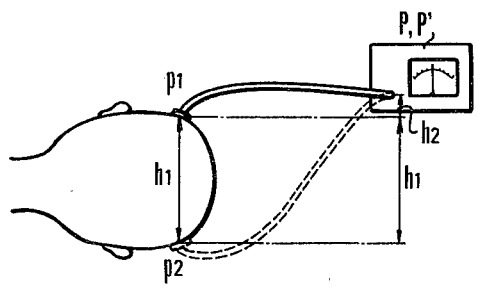

The present invention is described in detail with reference to the accompanying drawings, in which FIG. 1 shows a general side view to illustrate an embodiment of this invention inserted in a patient's head, FIG. 2 illustrates a relationship of the detected pressure vs. the internal volume of the pouch, FIG. 3 illustrates one detected pressure curve and another curve plotted from the detected pressure curve with a time delay, FIG. 4 shows a block diagram of another embodiment of this invention associated with automatic initial volume setting, FIG. 5 is a diagram to explain characteristics of this system to the turning of the patient's head.

Referring to FIG. 1 which is a schematic illustration of the intracranial pressure monitoring system, 1 is a scalp and 2 is a part of skull which has been cut out and is put back in the place after the craniotomy. Between the unremoved skull and the dura mater 3, a detector pouch 7 with a tube 8 is inserted before the cut out skull 2 is reset. End of the tube 8 is taken out through a burr hole 5 and sutured area 6 and connected to a measuring device comprising a manometer 9, a valve 10 and a liquid supplying source 11. The detector pouch is composed of considerably soft sheet such as polyethylene film, which is practically nonelastic within the range of intracranial pressure. The pouch is 1–3 cm in diameter, associated with a tube of 1–2 mm diameter. Such a soft pouch may be easily removed, if the internal liquid is discharged.

FIG. 2 shows a typical curve of the pressure to the internal volume of the pouch in the epidural region when varying its volume by injecting a liquid from the source 11 through a tube. It must be noted that the curve includes a noticeable plateau A. In accordance with experiments of inventors, it has been confirmed that the pressure in the pouch $P_o$ with the range of the plateau A is equal to the intracranial pressure $P_i$ with satisfactory accuracy. This fact may be explained by the following reason. When increasing the volume of the pouch, the contacting surface between the dura mater and the pouch is varied to be tuned into such a reasonable state at the plateau so as to transmit the intracranial pressure to the pouch pressure. Actually, if the contacting surface between the dura and pouch forms a plane or mean curvature of the contacting surface reduced to zero, the tensions of the dura and pouch do not give any effect to the difference between the pressures $P_i$ and $P_o$, i.e. $P_i = P_o$.

When pressure in the pouch reaches to the plateau A, the valve 10 in FIG. 1 is closed whereby an initial volume may be set and the liquid in the pouch-tube-transducer system is kept to a volume for maintaining the plateau. This means that the flat contact between dura and pouch is kept throughout the monitoring term, if each volume of the pouch, tube and the transducer is not effected by the change of intracranial pressure. In this situation, as a material of the pouch and tube, such an elastic material as latex is not naturally allowed because its shape is too much dependent on intracranial pressure. The same thing goes for such transducers as bellows-type, the volume of which change with intracranial pressure.

A simple and practical example of the automatic initial volume setting is realized as follows. In FIG. 3, a pressure curve accompanied by its time-delayed one are shown for the case of increasing the pouch volume. The two curves a and b approach together at their plateaus A and A', so that difference between the two pressures can be reduced to a level smaller than the preset reference pressure $\Delta P$. From this fact, an automatic setting of the volume may be realized by the system shown in FIG. 4. Liquid is supplied to the pouch through the solenoid operated valve 12 and its pressure is transformed by a pressure transducer 13 into the electrical signal. The signal is supplied to a voltage comparator 14 directly and through a delayed circuit 15, which correspond to the curves a and b in FIG. 3. When the difference is reduced to $\Delta P$, the comparator turns on and the amplifier 16 shuts down the solenoid valve 12. Another version of initial setting is also available using the circuit of FIG. 4 to discharge the liquid from the over-filled pouch. Anyway, after this procedure the valve remains closed to monitor the intracranial pressure.

By giving attention to the plateau of the pressure curve, simpler and more practical procedures are also available. In FIG. 2 it is observed that the initial volume to be set has a certain allowance. So the liquid of a predetermined proportion of the full volume of the pouch is enclosed in advance. If the pouch thus prepared is inserted and connected directly to the manometer 9, the intracranial pressure monitoring can be performed without any initial setting.

The intracranial pressure differs due to the referred position in the intracranial region. In FIG. 5, for example, the relation of the intracranial pressure $P_1$ of the upper position and $P_2$ of the lower position is $$P_2 = P_1 + \rho g h_1 \tag{1}$$

where $\rho$ gives the mean cerebral density and g the gravity acceleration. As mentioned earlier, the conventional methods show the pressure drift corresponding to $\rho g h_1$ (say roughly 100 mmH$_2$O) due to turning of the patients, while the normal intracranial measures are only about 150 mmH$_2$O.

In this invention, however, the pressue indications referred to the pressures P$_1$ and P$_2$ in FIG. 5 are given as $$P = P_1 - \rho' g h_2 \qquad (2)$$

and $$P' = P_2 - \rho' g (h_1 + h_2) \qquad (3)$$

respectively, where $\rho'$ is the density of the enclosed liquid. Combining the equations (1), (2) and (3), the remarkable relation is obtained as $$P = P' \qquad (4)$$

if the liquid density $\rho'$ is equal to the mean cerebral density $\rho$, which may be reasonably realized by adopting the saline as the enclosed liquid. Thus equation (4) assures a drift-free monitoring against the turning of patients. These are the remarkable features of this invention.

What is claimed is:

1. System for measuring intracranial pressure comprising
   a pouch consisting of a soft material which is non-elastic within the range of intracranial pressure, said pouch being of a size so as to allow its insertion between the skull and the cerebrum,
   said pouch being filled with a liquid for detecting the intracranial pressure,
   means for insuring no inflow and outflow displacement of the liquid in the pouch, and
   means for measuring the pressure of the liquid in said pouch, thereby detecting the intracranial pressure.

2. System for measuring intracranial pressure in accordance with claim 1 wherein
   said pouch has a flat surface constituting means for flatly contacting the dura mater when said pouch is in the space between the skull and dura mater with a sufficient volume of liquid in the pouch.

3. System for measuring intracranial pressure as set forth in claim 2, wherein
   the volume of the liquid in the pouch is in a flat region of the curve of detected pressure of the liquid vs. volume in the pouch, said detected pressure substantially equaling the intracranial pressure.

4. System for measuring intracranial pressure comprising
   a pouch consisting of a material which is non-elastic within the range of intracranial pressure for detecting the intracranial pressure, said pouch being of a size so as to allow its insertion between the skull and the cerebrum,
   a flexible tube connected to said pouch,
   means for supplying or discharging a liquid into or form said pouch through said tube, respectively,
   valve means for insuring no inflow and outflow displacement of the liquid in the pouch after supplying and during a measurement of the pressure thereof, and
   means connected to said tube for measuring the pressure of the liquid in said pouch and thereby detecting the intracranial pressure,
   said liquid having density equal to the mean cerebral density.

5. System for measuring intracranial pressure comprising
   a non-elastic pouch for detecting the intracranial pressure,
   means for supplying or discharging a liquid into or from said pouch,
   means for measuring the pressure of the liquid in said pouch,
   means for transforming said pressure of the liquid into an electrical signal,
   means for delaying said electrical signal for a predetermined period,
   means for comparing said electrical signal with said delayed electrical signal for emanating an output signal when difference between both electrical signals reaches to a predetermined small value, and
   means for stopping the supply or discharge of the liquid according to said output signal.

6. A method for measuring intracranial pressure comprising
   inserting a flat pouch consisting of a non-elastic material into the space between the skull and the cerebrum through a cut portion of the skull, with a flexible tube communicating with the pouch extending through the cut portion in the skull,
   supplying a liquid into the pouch through the flexible tube until a volume of liquid in the pouch is in a region where the detected pressure of the liquid in the pouch substantially equals the intracranial pressure, and
   detecting the pressure of the liquid in the pouch, thereby determining the intracranial pressure.

* * * * *

UNITED STATES PATENT AND TRADEMARK OFFICE
CERTIFICATE OF CORRECTION

PATENT NO. : 4,147,161

DATED : April 3, 1979

INVENTOR(S) : Jun Ikebe et al

It is certified that error appears in the above–identified patent and that said Letters Patent are hereby corrected as shown below:

CLAIM 4, LINE 10, "form" should be --from--

Signed and Sealed this

Twentieth Day of November 1979

[SEAL]

Attest:

RUTH C. MASON
Attesting Officer

LUTRELLE F. PARKER
Acting Commissioner of Patents and Trademarks